US006326522B1

(12) United States Patent
Nakaguchi et al.

(10) Patent No.: US 6,326,522 B1
(45) Date of Patent: Dec. 4, 2001

(54) PROCESS FOR PRODUCTION OF 1,3-DI(2-P-HYDROXYPHENYL-2-PROPYL)BENZENE

(75) Inventors: Toru Nakaguchi; Takafumi Tsujigami; Kenji Ekawa; Kenzo Tsujimoto; Kiyoshi Kumaki, all of Wakayama (JP)

(73) Assignee: Honshu Chemical Industry Co. Ltd., Tokyo (JP)

( * ) Notice: Subject to any disclaimer, the term of this patent is extended or adjusted under 35 U.S.C. 154(b) by 0 days.

(21) Appl. No.: 09/592,403

(22) Filed: Jun. 13, 2000

(30) Foreign Application Priority Data

Jun. 14, 1999 (JP) .................................................. 11-167554

(51) Int. Cl.$^7$ .................................................. C07L 39/12
(52) U.S. Cl. .................................................. 568/718
(58) Field of Search ................................................ 568/718

(56) References Cited

U.S. PATENT DOCUMENTS 3,393,244  7/1968  Broderick et al. .
3,979,462 * 9/1976  Krimm ................................. 568/718

FOREIGN PATENT DOCUMENTS 58-13528  1/1983  (JP) .

* cited by examiner

Primary Examiner—Michael L. Shippen
(74) Attorney, Agent, or Firm—Merchant & Gould P.C.

(57) ABSTRACT

The invention provides a process for production of 1,3-di (2-p-hydroxyphenyl-2-propyl)benzene which comprises:

reacting 1,3-di(2-hydroxy-2-propyl)benzene with phenol in an amount of 4–6 times in mols the amount of the 1,3-di(2-hydroxy-2-propyl)benzene in the presence of an acid catalyst at a temperature of 10–55° C. thereby crystallizing adducts formed of phenol and the resulting 1,3-di(2-p-hydroxyphenyl-2-propyl)benzene so that the reaction is effected in a slurry, and then recovering 1,3-di(2-p-hydroxyphenyl-2-propyl)benzene from the adduct.

5 Claims, No Drawings

PROCESS FOR PRODUCTION OF 1,3-DI(2-P-HYDROXYPHENYL-2-PROPYL)BENZENE

FIELD OF THE INVENTION

This invention relates to a process for production of a specific bisphenol compound, that is, 1,3-di(2-p-hydroxyphenyl-2-propyl)benzene.

DESCRIPTION OF PRIOR ART 1,3-Di(2-p-hydroxyphenyl-2-propyl)benzene is a kind of bisphenol compounds and is expressed by the structural formula (1):

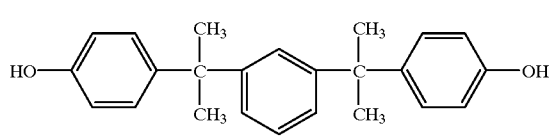

As described in U.S. Pat. No. 3,393,244, this compound is already known and is useful as a raw material for the production of thermoplastic polymers such as polycarbonates, polyesters or polysulfones, surface active agents, or stabilizers.

In general, 1,3-di(2-p-hydroxyphenyl-2-propyl)benzene is obtained by the reaction of 1,3-di(2-hydroxy-2-propyl)benzene having the formula (II)

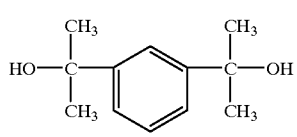

with an execess amount of phenol in the presence of an acid catalyst.

According to above-mentioned U.S. patent, the desired 1,3-di(2-p-hydroxyphenyl-2-propyl)benzene is obtained as follows. Phenol in an amount of 8–13 times in mols the amount of the compound (II) is placed in a reaction vessel and heated, and then hydrogen chloride gas is blown into the phenol so that the phenol is saturated therewith. Then, 1,3-di(2-hydroxy-2-propyl)benzene is added successively to the phenol at a temperature of 40–100° C., preferably at a temperature of 40–70° C. After the reaction, a large quantity of hot water is added to the resulting reaction mixture so that the desired reaction product is crystallized out of the resultant solution and filtered off.

On the other hand, according to Japanese Patent Laid-open No. 58-13528, the desired 1,3-di(2-p-hydroxyphenyl-2-propyl)benzene is obtained as follows. 1,3-Di(2-hydroxy-2-propyl)benzene, phenol in an amount of 2–10 times in mols the compound and a solvent (for example, benzene) are placed together with concentrated hydrochloric acid in a reaction vessel. The mixture is then allowed to react at a temperature in the range of –20° C. and 100° C. (for example, at a temperature of 5° C.). After the reaction, the resulting oil layer is separated from the reaction mixture and neutralized with an aqueous alkaline solution. The oil layer is washed with hot water to remove unreacted phenol therefrom, followed by cooling the layer to crystalize the desired compound (I).

However, according to the process of the U.S. patent, phenol is used in a high molar ratio to 1,3-di(2-hydroxy-2-propyl)benzene so that the process has problems that the volume efficiency of reaction vessel used is low and hence the process is poor in productivity when it is employed for industrial production of 1,3-di(2-p-hydroxyphenyl-2-propyl)benzene. Also according to the process of Japanese Patent Laid-open No. 58-13528, the process provides not a small amount of isomers or more highly condensed compounds such as five nuclear compounds. Accordingly, the known processes failed to produce the desired product, 1,3-di(2-p-hydroxyphenyl-2-propyl)benzene, in high selectivity.

The present inventors have made intensive investigation to solve such problems as involved in the known processes and found that when phenol is reacted with 1,3-di(2-hydroxy-2-propyl)benzene in a reduced molar ratio of phenol in the range of 4–6 to 1,3-di(2-hydroxy-2-propyl)benzene at a relatively low temperature in the presence of an acid catalyst, adducts are formed of phenol and the resulting 1,3-di(2-p-hydroxyphenyl-2-propyl)benzene and are crystallized out of the reaction mixture so that the reaction is thereafter allowed to proceed in a slurry, thereby suppressing the undesired by-production of isomers or highly condensed products such as five nuclear products and providing the desired 1,3-di(2-p-hydroxyphenyl-2-propyl)benzene in high selectivity and high yield.

Therefore, it is an object of the invention to provide a process for production of 1,3-di(2-p-hydroxyphenyl-2-propyl)benzene in high selectivity and high yield with reduced by-production of isomers or highly condensed products such as five nuclear products.

SUMMARY OF THE INVENTION

The invention provides a process for production of 1,3-di(2-p-hydroxyphenyl-2-propyl)benzene which comprises:

reacting 1,3-di(2-p-hydroxyphenyl-2-propyl)benzene with phenol in an amount of 4–6 times in mols the amount of the 1,3-di(2-p-hydroxyphenyl-2-propyl)benzene in the presence of an acid catalyst at a temperature of 10–55° C. thereby crystallizing adducts formed of phenol and the resulting 1,3-di(2-p-hydroxyphenyl-2-propyl)benzene out of the reaction mixture so that the reaction is effected in a slurry, and then recovering 1,3-di(2-p-hydroxyphenyl-2-propyl)benzene from the adduct.

DESCRIPTION OF PREFERRED EMBODIMENTS

According to the process of the invention, 1,3-di(2-hydroxy-2-propyl)benzene is reacted with phenol in an amount of 4–6 times in mols, preferably in an amount of 5.0–5.5 times in mols, the amount of 1,3-di(2-hydroxy-2-propyl)benzene, in the presence of an acid catalyst at a temperature of 10–55° C., preferably at a temperature of 20–50° C., more preferably at a temperature of 30–50° C., thereby crystallizing adducts formed of phenol and 1,3-di(2-p-hydroxyphenyl-2-propyl)benzene out of the reaction mixture so that the reaction is effected in a slurry, and then the adduct is treated to recover the desired 1,3-di(2-p-hydroxyphenyl-2-propyl)benzene.

In a preferred embodiment of the invention, phenol is placed in a reaction vessel, and hydrogen chloride gas is blown thereinto to saturate the phenol therewith, or concentrated hydrochloric acid (having a concentration of not less than 35% by weight) is added to phenol and then hydrogen chloride gas is blown thereinto to saturate the phenol therewith. Thereafter, 1,3-di(2-hydroxy-2-propyl)benzene and if necessary phenol are added successively to the phenol in the reaction vessel with stirring, and after the addition of 1,3-di(2-hydroxy-2-propyl)benzene, the mixture is further stirred to effect a post-reaction.

When 1,3-di(2-hydroxy-2-propyl)benzene is added to the phenol in the reaction vessel as mentioned above, it is preferred that a portion (preferably 50–80 mol %) of phenol to be reacted with 1,3-di(2-hydroxy-2-propyl)benzene is in advance separated and a mixture is prepared by mixing the portion with 1,3-di(2-hydroxy-2-propyl)benzene in the form of solution or slurry, and the mixture is added successively to the rest of the phenol placed in the reaction vessel.

According to the process of the invention, while 1,3-di(2-hydroxy-2-propyl)benzene (and phenol) is added successively to the phenol in the reaction vessel or while the post-reaction is carried out after the addition of 1,3-di(2-hydroxy-2-propyl)benzene, adducts are formed of phenol and 1,3-di(2-p-hydroxyphenyl-2-propyl)benzene formed in the reaction and the adducts are crystallized out of the reaction mixture so that the reaction mixture becomes a slurry, so that, thereafter, the reaction is allowed to proceed in a slurry.

Thus, according to the invention, the desired reaction product or 1,3-di(2-p-hydroxyphenyl-2-propyl)benzene is crystallized or deposited as adducts with phenol out of the reaction mixture and after the adducts are once crystallized, the reaction is carried out in a slurry. It is believed that, because the reaction is effected in a slurry as mentioned above, undesirable side reactions such as isomerization or higher condensation of the desired product to form five nuclear products is suppressed and the reaction yield improves.

As clear from the foregoing, the use of hydrocarbon solvents such as toluene or benzene in which 1,3-di(2-p-hydroxyphenyl-2-propyl)benzene is soluble should be avoided in the process of the invention.

In the meantime, an effective amount of seed crystals (or crystallization nucleating agents) to promote the crystallization of the adduct, such as preferably 1,3-di(2-p-hydroxyphenyl-2-propyl)benzene or its adducts with phenol, may be in advance added to the reaction mixture, or they may be added to the reaction mixture when 1,3-di(2-hydroxy-2-propyl)benzene is added to phenol. The amount of the seed crystals is not specifically limited, but it is usually in the range of 0.1–10% by weight in relation to the amount of phenol used.

In many cases, while 1,3-di(2-hydroxy-2-propyl)benzene is added successively to the phenol in the reaction vessel or while the post-reaction is carried out after the addition of 1,3-di(2-hydroxy-2-propyl)benzene, the adduct is crystallized out of the reaction mixture so that the reaction mixture becomes a slurry. Thus, as the reaction proceeds, the viscosity of the reaction mixture becomes high and it becomes difficult to stir the reaction mixture effectively.

Therefore, according to the invention, it is preferred that 1,3-di(2-hydroxy-2-propyl)benzene is added successively to the phenol in the reaction vessel at a temperature of 30–45° C., and after the addition, the post-reaction is carried out with stirring at a temperature higher than the above temperature and in the range of 40–55° C.

The adduct formed of phenol and 1,3-di(2-p-hydroxyphenyl-2-propyl)benzene in the reaction as described above has usually a molar ratio of 1:1, however, the molar ratio in the adduct is not specifically limited thereto.

After the post-reaction is effected as mentioned above, the desired product, 1,3-di(2-p-hydroxyphenyl-2-propyl)benzene is recovered from the adduct formed of phenol and 1,3-di(2-p-hydroxy-phenyl-2-propyl)benzene.

According to a preferred embodiment of the process of the invention, an aqueous alkaline solution is added to a slurry containing the adduct to neutralize the acid catalyst used, and the resulting aqueous layer is separated. Water is added to the resulting oil layer to effect crystallization, followed by collecting the resulting adducts formed of phenol and 1,3-di(2-p-hydroxyphenyl-2-propyl)benzene as primary crystals by filtering the reaction mixture. The primary crystals are then subjected to distillation under reduced pressure to recover phenol and a crystallization solvent is added to the distillation residue to effect crystallization of the desired product, followed by collecting the product by filtering and drying the product.

Alternatively, the oil layer is washed with distilled water, and the resulting aqueous layer is separated. The resulting oil layer is subjected to distillation under reduced pressure to recover phenol and then a crystallization solvent is added to the distillation residue to effect crystallization of the desired product and the product is collected as primary crystals by filtering. The primary crystals are dissolved in a crystallization solvent, followed by crystallization and collecting the product by filtering and drying the product. By these operations the desired product is obtained in high purity.

The aqueous alkaline solution used in the above process for recovery the desired product is not specifically limited, but alkali metal hydroxides such as sodium hydroxide or potassium hydroxide, or alkali metal carbonates such as sodium carbonate or potassium carbonate are usually used. The crystallization solvent used is also not specifically limited, but aromatic hydrocarbon solvents such as benzene, toluene or xylene, or aliphatic hydrocarbon solvents such as pentane, hexane or heptane are usually used.

However, the process to recover 1,3-di(2-p-hydroxyphenyl-2-propyl)benzene from the adduct is not specifically limited to the above-exemplified one, and the desired product may be otherwise recovered from the adduct.

As set forth above, according to the process of the invention, 1,3-di(2-hydroxy-2-propyl)benzene is reacted with phenol in the presence of an acid catalyst so that adducts are formed of phenol and the resulting 1,3-di(2-p-hydroxyphenyl-2-propyl)benzene and are crystallized out of the reaction mixture and the reaction is effected in a slurry, and then the desired 1,3-di(2-p-hydroxyphenyl-2-propyl)benzene is recovered from the adduct. Therefore, the desired product is obtained in high selectivity and in high yield while suppresing undesired by-production of isomers or highly condensed products.

The invention will now be described in more detail with reference to examples, however, the invention is not limited thereto.

EXAMPLE 1

75.2 g (0.8 mol) of phenol and 15.0 g of 35% hydrochloric acid were placed in a four necked one liter capacity flask and hydrogen chloride gas was blown into the phenol to saturate the phenol therewith.

A mixed solution of 77.6 g (0.4 mol) of 1,3-di(2-hydroxy-2-propyl)benzene and 112.8 g (1.2 mol) of phenol was added dropwise from a 300 mL capacity dropping funnel to the phenol in the flask at a temperature of 30° C. for four hours, and a post-reaction was carried out at the same temperature.

When the post-reaction was carried out for one hour, crystals were formed. Then the reaction temperature was raised to 45° C. and the reaction was effected in a slurry. In this way, the reaction was carried out for nine hours from the start of the dropwise addition of the mixture of 1,3-di(2-hydroxy-2-propyl)benzene and phenol.

After the reaction completed, a 16% aqueous solution of sodium hydroxide was added to the resulting reaction mixture to neutralize it. The resulting aqueous layer was separated and the resulting oil layer was subjected to quantitative analysis of 1,3-di(2-p-hydroxyphenyl-2-propyl)benzene in the oil layer by means of high performance liquid chromatography (HPLC) to show that 125.3 g of the desired product were formed or the reaction yield was 90.5 mol % based on 1,3-di(2-hydroxy-2-propyl)benzene used.

100 g of distilled water were added to the oil layer and the resulting crystals were filtered off to provide 150.0 g of white primary crystals. The analysis of the primary crystals showed that they were comprised of 68.9% (103.8 g) of 1,3-di(2-p-hydroxyphenyl-2-propyl)benzene, 21.8% (32.9 g) of phenol and 9.3% (14.0 g) of water, and that they were adducts formed of phenol and 1,3-di(2-p-hydroxyphenyl-2-propyl)benzene in an equimolar ratio. The yield (crude yield) of the primary crystals was found to be 75.0 mol % based on 1,3-di(2-hydroxy-2-propyl)benzene.

After the recovery of phenol from 150.7 g of the primary crystals by distillation under reduced pressure, 230 g of toluene and 17 g of distilled water were added to the distillation residue to effect crystallization. The crystals were filtered off and dried to provide 98.6 g of the desired product having a purity of 99.8%. The yield of the desired product was found to be 71.2 mol % based on 1,3-di(2-hydroxy-2-propyl)benzene.

EXAMPLE 2

75.2 g (0.8 mol) of phenol and 15.0 g of 35% hydrochloric acid were placed in a four necked one liter capacity flask and hydrogen chloride gas was blown into the phenol to saturate the phenol therewith.

A mixed solution of 77.6 g (0.4 mol) of 1,3-di(2-hydroxy-2-propyl)benzene and 112.8 g (1.2 mol) of phenol was added dropwise from a 300 mL capacity dropping funnel to the phenol in the flask at a temperature of 45° C. for four hours, and a post-reaction was carried out at the same temperature. When the post-reaction was carried out for one hour, crystals were formed. Then the reaction was effected in a slurry. In this way, the reaction was carried out for nine hours from the start of the dropwise addition of the mixture of 1,3-di(2-hydroxy-2-propyl)benzene and phenol.

Thereafter in the same manner as in Example 1, the desired product, 1,3-di(2-p-hydroxyphenyl-2-propyl)benzene was obtained in a yield of 74.0 mol %. The reaction yield was 92.9 mol % and the crude yield was 78.2 mol %.

EXAMPLE 3

37.6 g (0.4 mol) of phenol and 17.5 g of 35% hydrochloric acid were placed in a four necked one liter capacity flask and hydrogen chloride gas was blown into the phenol to saturate the phenol therewith.

A mixed solution of 77.6 g (0.4 mol) of 1,3-di(2-hydroxy-2-propyl)benzene and 112.8 g (1.2 mol) of phenol was added dropwise from a 300 mL capacity dropping funnel to the phenol in the flask at a temperature of 30° C. After two hours from the start of the addition, crystallization bagan so that the reaction temperature was raised to 55° C., and thereafter the reaction was carried out in a slurry.

In this way, the reaction was carried out for nine hours from the start of the dropwise addition of the mixture of 1,3-di(2-hydroxy-2-propyl)benzene and phenol.

After the reaction completed, a 16% aqueous solution of sodium hydroxide was added to the resulting reaction mixture to neutralize it. The resulting aqueous layer was separated and the resulting oil layer was subjected to quantitative analysis of 1,3-di(2-p-hydroxyphenyl-2-propyl)benzene in the oil layer by means of HPLC to show that 126.9 g of the desired product were formed. The reaction yield was found to be 91.7 mol % based on 1,3-di(2-hydroxy-2-propyl)benzene used.

The resulting oil layer was washed with 100 g of distilled water and the aqueous layer was separated. The resulting oil layer was subjected to distillation under reduced pressure to recover phenol therefrom. 273.4 g of toluene and 20.5 g of distilled water were added to the distillation residue and the resulting crystals were filtered off and dried to provide the desired product in a yield of 82.5 mol % based on 1,3-di(2-hydroxy-2-propyl)benzene.

EXAMPLE 4

37.6 g (0.4 mol) of phenol and 17.5 g of 35% hydrochloric acid were placed in a four necked one liter capacity flask and hydrogen chloride gas was blown into the phenol to saturate the phenol therewith.

A mixed solution of 77.6 g (0.4 mol) of 1,3-di(2-hydroxy-2-propyl)benzene and 150.4 g (1.6 mol) of phenol was added dropwise from a 300 mL capacity dropping funnel to the phenol in the flask at a temperature of 30° C. After two hours from the start of the addition, crystallization bagan and the reaction temperature was raised to 55° C., and thereafter the reaction was carried out in a slurry. In this way, the reaction was carried out for nine hours from the start of the dropwise addition of the mixture of 1,3-di(2-hydroxy-2-propyl)benzene and phenol.

After the reaction, a 16% aqueous solution of sodium hydroxide was added to the resulting reaction mixture to neutralize it. The resulting aqueous layer was separated and the resulting oil layer was subjected to quantitative analysis of 1,3-di(2-p-hydroxyphenyl-2-propyl)benzene in the oil layer by means of HPLC to show that 127.6 g of the desired product were formed. The reaction yield was found to be 92.2 mol % based on 1,3-di(2-hydroxy-2-propyl)benzene used.

The resulting oil layer was washed with 100 g of distilled water and the aqueous layer was separated. The resulting oil layer was subjected to distillation under reduced pressure to recover phenol therefrom. 273.4 g of toluene and 20.5 g of distilled water were added to the distillation residue and the resulting crystals were filtered off and dried to provide the desired product having a purity of 99.8% in a yield of 83.3 mol % based on 1,3-di(2-hydroxy-2-propyl)benzene.

Comparative Example 1

75.2 g (0.8 mol) of phenol and 22.5 g of sulfonic acid type ion exchange resin (Amberlist 15) were placed in a four necked one liter capacity flask.

A mixed solution of 77.6 g (0.4 mol) of 1,3-di(2-hydroxy-2-propyl)benzene and 150.4 g (1.6 mol) of phenol was added dropwise from a 300 mL capacity dropping funnel to the phenol in the flask at a temperature of 45° C. for four hours. After the addition, a post-reaction was effected at the same temperature for five hours. Throughout the reaction, however, the reaction mixture was remained solution and no crystallization took place.

After the reaction, the resulting reaction mixture was subjected to quantitative analysis of 1,3-di(2-p-hydroxyphenyl-2-propyl)benzene therein by means of HPLC to show that 65.0 g of the desired product were formed in a reaction yield of 47.0 mol % based on 1,3-di(2-hydroxy-2-propyl)benzene used.

Comparative Example 2

47.0 g (0.5 mol) of phenol, 19.4 g (0.1 mol) of 1,3-di(2-hydroxy-2-propyl)benzene and 80.0 g of toluene were placed in a four necked 300 mL capacity flask.

100 g of 35% hydrochloric acid were added to the mixture at a temperature of 5° C. and the reaction was carried out for ten hours at the same temperature. Throughout the reaction, the reaction mixture was remained solution and no crystallization took place.

After the reaction, an oil layer was separated from the resulting reaction mixture. A 18% aqueous solution of sodium hydroxide was added to the oil layer to neutralize it. The resulting aqueous layer was separated and the resulting oil layer was washed with 50 g of distilled water, and the aqueous layer was separated. The oil layer was subjected to quantitative analysis of 1,3-di(2-p-hydroxyphenyl-2-propyl)benzene therein by means of HPLC to show that 14.5 g of the desired product were formed in a reaction yield of 41.8 mol % based on 1,3-di(2-hydroxy-2-propyl)benzene used.

What is claimed is:

1. A process for production of 1,3-di(2-p-hydroxyphenyl-2-propyl)benzene which comprises:

reacting 1,3-di(2-hydroxy-2-propyl)benzene with phenol in an amount of 4–6 times in mols the amount of the 1,3-di(2-hydroxy-2-propyl)benzene in the presence of an acid catalyst at a temperature of 10–55° C. thereby crystallizing adducts formed of phenol and the resulting 1,3-di(2-p-hydroxyphenyl-2-propyl)benzene so that the reaction is effected in a slurry, and then recovering 1,3-di(2-p-hydroxyphenyl-2-propyl)benzene from the adduct.

2. The process as claimed in claim 1 wherein phenol is used in an amount of 5.0–5.5 times in mols the amount of 1,3-di(2-hydroxy-2-propyl)benzene.

3. The process as claimed in claim 1 wherein 1,3-di(2-hydroxy-2-propyl)benzene is added successively to phenol containing an acid catalyst at a temperature of 10–50° C., and then the reaction is effected at a temperature higher than the above temperature and in the range of 40–55° C.

4. The process as claimed in claim 1 wherein the acid catalyst is hydrogen chloride gas and/or concentrated hydrochloric acid.

5. The process as claimed in claim 1 wherein 1,3-di(2-hydroxy-2-propyl)benzene is reacted with phenol in the presence of seed crystals of 1,3-di(2-p-hydroxyphenyl-2-propyl)benzene or adducts formed of phenol and 1,3-di(2-p-hydroxyphenyl-2-propyl)benzene.

\* \* \* \* \*